United States Patent [19]

Lancaster, Jr. et al.

[11] Patent Number: 4,758,227

[45] Date of Patent: Jul. 19, 1988

[54] BIRD INJECTION SYSTEM

[75] Inventors: Gordon J. Lancaster, Jr.; Joey T. Stump, both of Bent Mountain; William M. Marshall, Sr., Salem, all of Va.

[73] Assignee: Morf Inc., Salem, Va.

[21] Appl. No.: 914,809

[22] Filed: Oct. 3, 1986

Related U.S. Application Data

[63] Continuation-in-part of Ser. No. 779,221, Sep. 24, 1983, abandoned.

[51] Int. Cl.[4] .......... A61M 5/00

[52] U.S. Cl. .......... 604/144; 604/156

[58] Field of Search .......... 604/156, 144, 143, 145, 604/147, 131, 136-139, 152

[56] References Cited

U.S. PATENT DOCUMENTS

| | | | |
|---|---|---|---|
| 2,782,682 | 2/1957 | Browning et al. | 604/156 X |
| 3,964,481 | 6/1976 | Gourlandt et al. | 604/156 X |
| 4,108,176 | 8/1978 | Walden | 604/147 X |
| 4,276,879 | 7/1981 | Yiournas | 604/156 X |
| 4,515,590 | 5/1985 | Daniel | 604/156 |

*Primary Examiner*—Stephen C. Pellegrino

*Attorney, Agent, or Firm*—John F. C. Glenn

[57] ABSTRACT

A bird is positively positioned in a fixed cradle and a motor drives injection needles at convergent angles into the bird's breast muscle tissue on opposite sides of the keel bone, actuates injection, and retracts the needles. Starting is initiated by the operator's hand which grasps the bird's legs.

10 Claims, 7 Drawing Sheets

BIRD INJECTION SYSTEM

This is a continuation-in-part of application Ser. No. 779,221 filed Sept. 24, 1985, now abandoned, by Gordon J. Lancaster, Jr. and Joey Thomas Stump.

BACKGROUND OF THE INVENTION

When chickens or other birds require injections these must be administered quickly, to save time and also carefully to make sure they reach only breast muscle tissue. Otherwise, the dosage may be ineffective, or the bird may be injured or killed by being stabbed in a vital organ, or the person administering the injection may inadvertently inject himself, which is not only painful but also may be serious medically.

SUMMARY OF THE INVENTION

In accordance with the present invention, a stationary cradle holds a chicken, turkey or other fowl or bird with its breast facing downwardly and centered in a predetermined fixed position, while the operator places one hand on the bird and the other hand about its legs projecting downwardly from the cradle. The cradle has means along its sides to limit sidewise movement of the bird, means across opposite ends to limit endwise movement of the bird, and means at one end to divide the legs on opposite sides of the lengthwise centerline of the cradle. A switch to actuate an automatic injection cycle is positioned beneath the cradle where it can readily be pressed open by the hand grasping the legs of the bird. One or both of a pair of upwardly extending injection needles are mounted beneath the cradle for upward convergent movement into the breast muscle tissue on opposite sides of the keel bone of a bird's breast positioned in the cradle, until each needle reaches the breast muscle at which it is aimed. Syringes are then activated to inject dosages through the needles, and thereafter the needles are withdrawn and the syringes refilled. The cycle stops the apparatus where it began, ready for the next cycle.

Other objects, advantages and details will become apparent as the following disclosure proceeds.

BRIEF DESCRIPTION OF THE DRAWINGS

The accompanying drawings semi-schematically illustrate initial and current apparatus of the invention, as follows.

DETAILED DESCRIPTION OF PRESENT PREFERRED EMBODIMENTS

Figure 1:
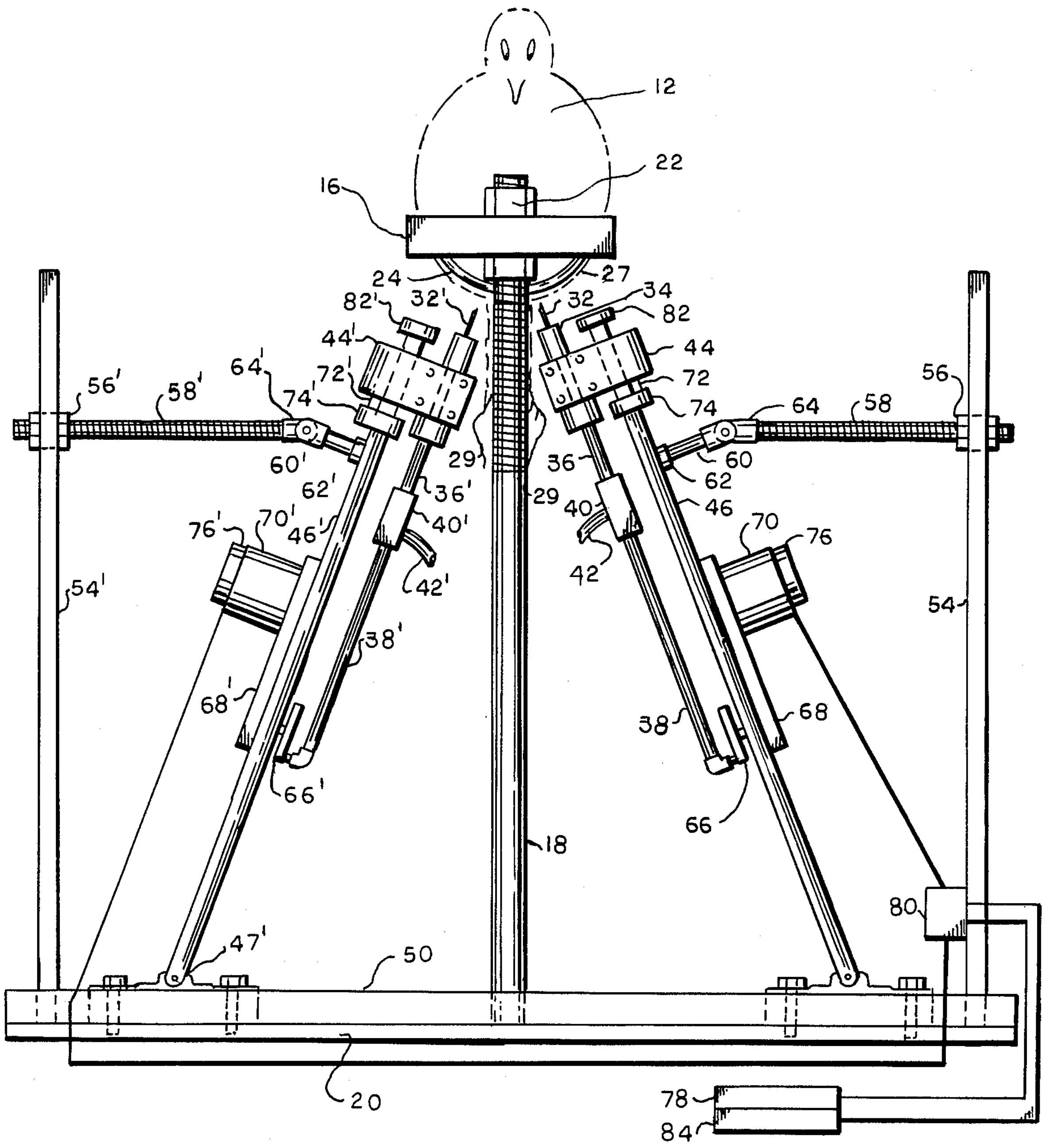
FIG. 1 shows a front view of a bird (in phantom lines) positioned in apparatus of the invention.

Referring now to the drawings, the earlier embodiment of the invention shown in FIGS. 1–4 has a cradle 10 on which a chicken 12 may be placed with its breast in a position determined by the position and shape of the cradle.

Figure 2A:
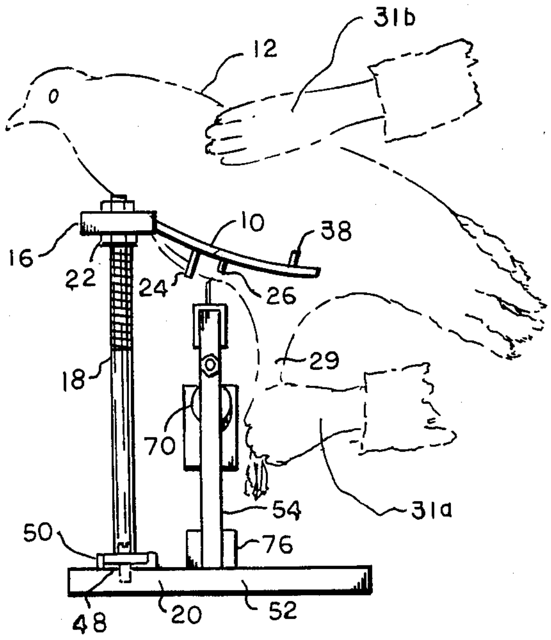
FIG. 2A shows a view from the right side of what is shown in FIG. 1, in reduced scale.
Figure 2B:
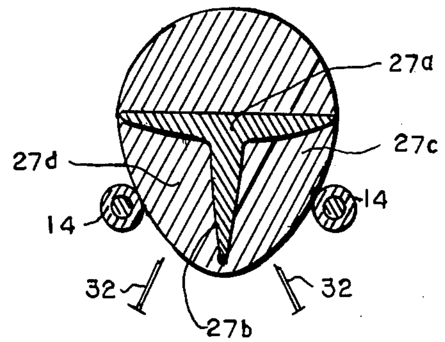
FIG. 2B shows a section through the chicken breast bone and breast muscle tissue, and the injection needles aimed at the breast, as seen from the direction of FIG. 1.
Figure 3:
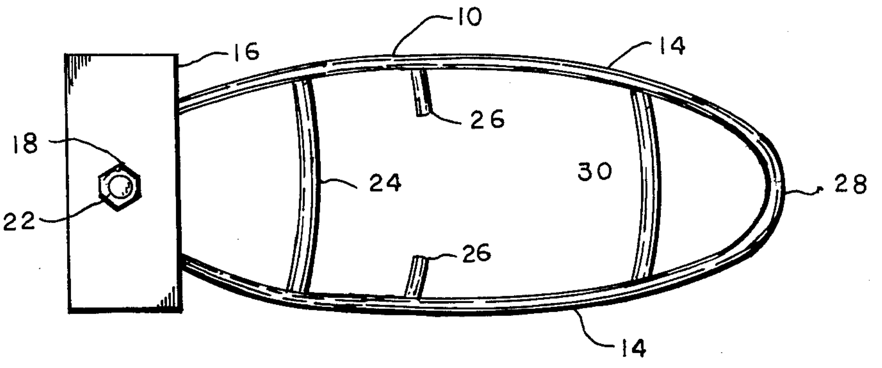
FIG. 3 shows a top plan view of the cradle holding the chicken shown in FIGS. 1 and 2, with the chicken removed.
Figure 4:
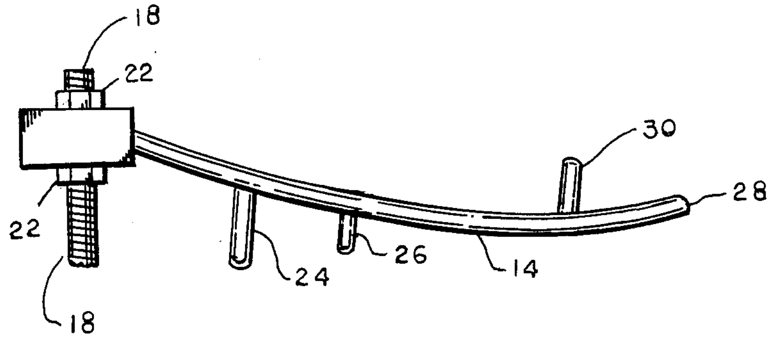
FIG. 4 shows a side view of what is shown in FIG. 3.

The cradle 10 has a downwardly sloping open frame (FIGS. 3 and 4) comprising a generally U-shaped tubular member 14 secured at its free ends to a block 16 which forms the forward end of the cradle and is carried by a threaded post 18 extending up from a base 20. A pair of nuts 22 lock the block 16 on post 18 and are adjustable to move the block up and down on the post. The tubular cross member 24 curves in a downwardly extending semicircle between opposite sides of member 14. A pair of short tubular members 26 extend generally toward each other from opposite sides of member 14 and slope downwardly like the end portions of member 24. These cradle frame members 24 and 26 cooperate to hold successive birds of approximately the same size with the bird's breast 27 in a substantially horizontal position with the breast facing downwardly and the forward end of the breast bone **27*a* abutting block 16. The bird's legs 29 extend over opposite sides of the curved end 28 of the U-shaped member 14. This positioning is aided by supplemental member 30 extending upwardly in a semicircle between opposite sides of member 14 between its curved end 28 and members 26. The supplemental member 30 limits endwise movement of the bird toward its tail and also helps to divide the legs of the bird in the cradle and position them to be grasped by one hand 31*a* of an operator while the other hand 31*b* is place over back of the bird between its wings. The bird is thus positioned with the keel bone 27*b* of the breast bone 27*a* extending straight down and aligned lengthwise with the lengthwise center line of the cradle as a result of being centered between the sides of U-shaped frame member 14** (FIG. 2B).

Referring now to the right side of FIG. 1, an injection needle 32 extends from a conventional bird injection syringe 34 having a plunger (not shown) operated by a hollow push rod 36 for ejecting fluid from the syringe through the needle. A second push rod 38 is aligned with the push rod 36 and is connected to and aligned with a second plunger (not shown) in a cylinder 40. Syringe 34 receives replenishing fluid from cylinder 40 through the inside of rod 36, and a flexible plastic tube 42 connects cylinder 40 to suck in fluid from a supply container (not shown). The syringe 34 and cylinder 40 each have a compression spring inside (not shown) to return the plungers to their down positions, and each has internal valving (not shown) whereby the syringe ejects fluid through the needle 32 on the up strokes of rods 36 and 38, and receives a replenishing charge from cylinder 40 on the down strokes while cylinder 40 draws in fluid through tube 42 on said up strokes and ejects fluid to replenish syringe 34 on said down strokes.

A collar 44 is clamped rigidly but adjustably around the upper end of syringe 34, and also extends slideably around the upper end of a support rod 46. The bottom of rod 46 is pivotally connected by a pin 47 to a plate 48 which is horizontally slideable between two parallel rails 50 fixed on base 20 until it is secured to the base in a desired position. A vertical post 54 is anchored at its lower end in base 20 and near its upper end pivotally supports a nut 56 screwed around one end of a rod 58 extending generally horizontally toward support rod 46. The pivotal mount of nut 56 permits rod 58 to swing vertically. A short connecting rod 60 is held by a socket 62 secured to an upper portion of rod 46, but is free to rotate in socket 62. A universal joint 64 connects the other ends of rods 58 and 60. Rod 58 is rotatable in nut 56, and plate 48 is independently slideable between rails 50 to swing support rod 46 about pin 47 in a plane passing through the position of the breast muscles of a bird in cradle 10.

The lower end of push rod 38 is pinned to the periphery of a drive wheel 66 which is driven through reduction gear box 68 by an electric motor 70. The motor is stopped when collar 44 slides down rod 46 and electrically connected to stop motor 70. A magnetic brake 76 is also activated by switch 74 when it stops motor 70, so as to stop drive wheel 66 where push rod 38 moves down to its lowermost position. Motor 70 is started and magnetic brake 76 is released by pressing a foot pedal 78. This pedal is operatively connected to the motor and brake through a circuit including a capacitor 80.

A stop 82 at the top of rod 46 is engaged by collar 44, after push rods 36 and 38 have been driven up to carry collar 44 up with them, and meanwhile to drive needle 32 into the breast muscle **27*c* of a bird positioned in cradle 10, on the same side of the keel bone 27*b* as the side beneath which needle 32 is positioned. This insertion of the needle occurs without deflection of the springs in syringe 34 and cylinder 40, which are made strong enough for that purpose. After collar 44 engages stop 82, continued upward movement of rods 38 and 36 through action of drive wheel 66 causes the springs to deflect and syringe 34 to eject through needle 32 while cylinder 40 is replenished as previously described. Drive wheel 66 continues its rotation at the end of this upward movement and starts retraction of push rods 38 and 36 in conjunction with the pressure of the compressed springs. When collar 44 hits stop switch feeler 72** the motor stops, the brake engages and the cycle is completed, ready for the next cycle.

Another needle 32' is mounted on the other side of cradle 10, to inject the breast muscle tissue **27*d* on the other side of the keel bone of chicken 12. The needles 31 and 32' are mounted symmetrically on opposite sides of a vertical plane through the fore-and-aft centerline through cradle 10 and the keel bone of a bird in cradle 10, so that the lines of movement of the needles converge toward that plane. Needle 32' is mounted and operated by members corresponding to the members with numbers from 34 to 82 (except 50, 52, and 80 which are used in common). This is indicated by designation numbers which correspond but are shown with a following prime mark. The motor 70' is similarly controlled by a pedal 84, which is placed next to the pedal 78 so that they can be operated simultaneously when both needles 32 and 32' are to inject simultaneously. If only one needle is to inject, its pedal is separately operated. The capacitor 80 is connected to operate with both of the motors 70 and 70'**.

The current and present preferred embodiment of the invention is shown in FIGS. 5–14. It has a bird-positioning cradle 90 comprising a block 92 secured between the ends of a generally U-shaped frame 94 of sheet metal. The frame 94 has sides 96 and 98 which are slanted to converge downwardly where they extend between block 92 and the frame end section 100 extending between the projecting ends of frame sides 96 and 98. End section 100 projects upwardly in a convex curve along its top edge, to facilitate dividing the legs 97 of a bird 99 in the cradle and thereby rotationally positioning the breast of the bird to face downwardly with the keel bone vertical and centered in the middle of the cradle when the bird's legs are held substantially straight down. The end section 100 is preferably reinforced by a like additional section (not shown) secured to it. The lower edges of frame sides 96 and 98 extend relatively far down and hence relatively close to each other along the portions 102 and 104 of sides 96 and 98 extending forward from end section 100 about halfway toward block 92. The side portions 102 and 104 thus slope toward each other for cooperating with section 100 in rotationally positioning the bird's breast as just described. Frame sides 96 and 98 are notched underneath at 106 and 108 from about halfway between block 92 and end member 100 most of the way toward block 92, in order to expose more area of the bird's breast where injection needles are to be inserted. Block 92 has an edge 110 between frame sides 96 and 98 and facing end section 100. Edge 110 is adapted to abutt the front end of the breast bone of a bird being placed in the cradle, thereby causing the breast of the bird to be placed in the cradle where the portion of its breast to be injected is in a predetermined position between notched edges 106 and 108 and thus ready for injection by needles 112 and 114 mounted beneath cradle 90 in symmetrically offset relation to a vertical plane through the keel bone of the bird in the cradle.

Needles 112 and 114 extend from syringes 116 and 118 carried in separate assemblies 120 and 122 mounted for independent angular and laterally adjustment relative to a common base plate 124. Assembly 120 is beneath and to the right of cradle 90 as viewed in FIGS. 5 and 9, and assembly 122 is beneath and to the left of cradle 90, as viewed in those figures and also as viewed by an operator standing in position to use the apparatus.

Referring first to assembly 120 (FIGS. 5 and 9–13), it is supported by and mostly contained within a rigid sheet metal cover 124 with one side 126 secured to an adjacent vertical support plate 128. Cover 124 and plate 128 are positioned between and horizontally moveable along a pair of spaced parallel upturned edges 134 and 136 of a horizontal channel member 138 mounted on base plate 124. The lower end of plate 128 lies against the inner side of flange 134 and is secured thereto by a short bolt 140 extending through a horizontal slot 142 in flange 134. The head of bolt 140 bears against the inner face of plate 128 and its threaded end is screwed into a knob 144 against the outer face of flange 134. Knob 144 can be turned one way to cause bolt 140 to press plate 128 against flange 134, and the other way to allow bolt 140 to move along slot 142 while plate 128 and assembly cover 124 move horizontally along channel member 138.

Assembly cover 124 is rotationally adjustable by pivotal movement about a long bolt 146 extending horizontally from its head against the outside of flange 136, through a horizontal slot 148 in flange 136, through close fitting openings through opposite sides of cover 124, through a close fitting opening through plate 128, through a horizontal slot 150 in flange 134, and at its threaded far end into a threaded opening in a knob 152 against the outer side of flange 134. Knob 152 is turned one way to tighten bolt 146 against the members that holds it together, and the other way to loosen the grip of bolt 146. One function of bolt 146 is to pivotally support assembly cover 124, and another function is to cooperate with bolt 140 in locking plate 128 in fixed position on channel 138 when both bolts are tightened. When loosened, both bolts slide along slot 138 (and bolt 146 slides along slot 148) for purposes of lateral adjustment of the position of plate 128, carrying with it assembly cover 124.

Cover 124 is locked against pivotal movement by a bolt 154 extending horizontally through an arcuate slot 156 in the upper end of plate 128. Bolt 154 has its head against the inner side of cover 126, and its far end fixed in a knob 158. The arcuate curve of slot 156 is centered on bolt 146. When knob 158 is turned one way it locks cover side 126 against plate 128, thus preventing any pivotal movement of cover 124. When turned the other way knob 158 releases cover 124 for pivotal movement about bolt 146. Thus, knob 158 is operable to permit needle 112 to swing to a desired angular position, and then to lock it in that position.

Figure 5:
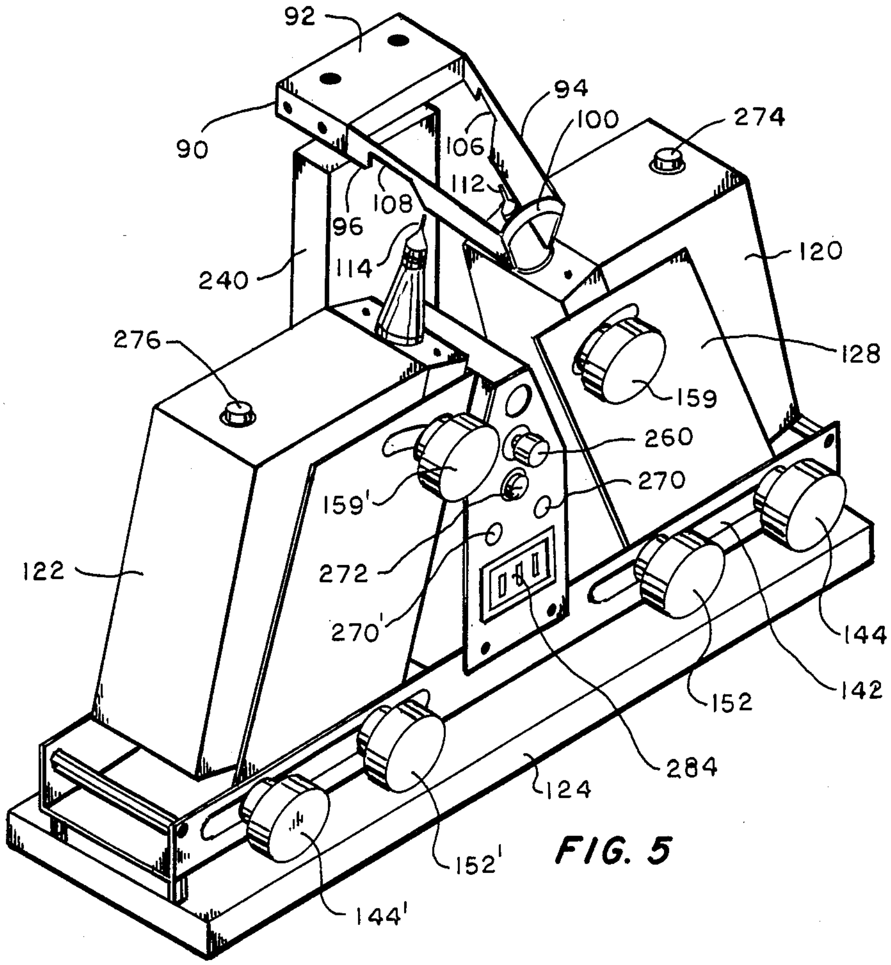
FIG. 5 shows an isometric perspective view of improved apparatus of the invention.
Figure 9:
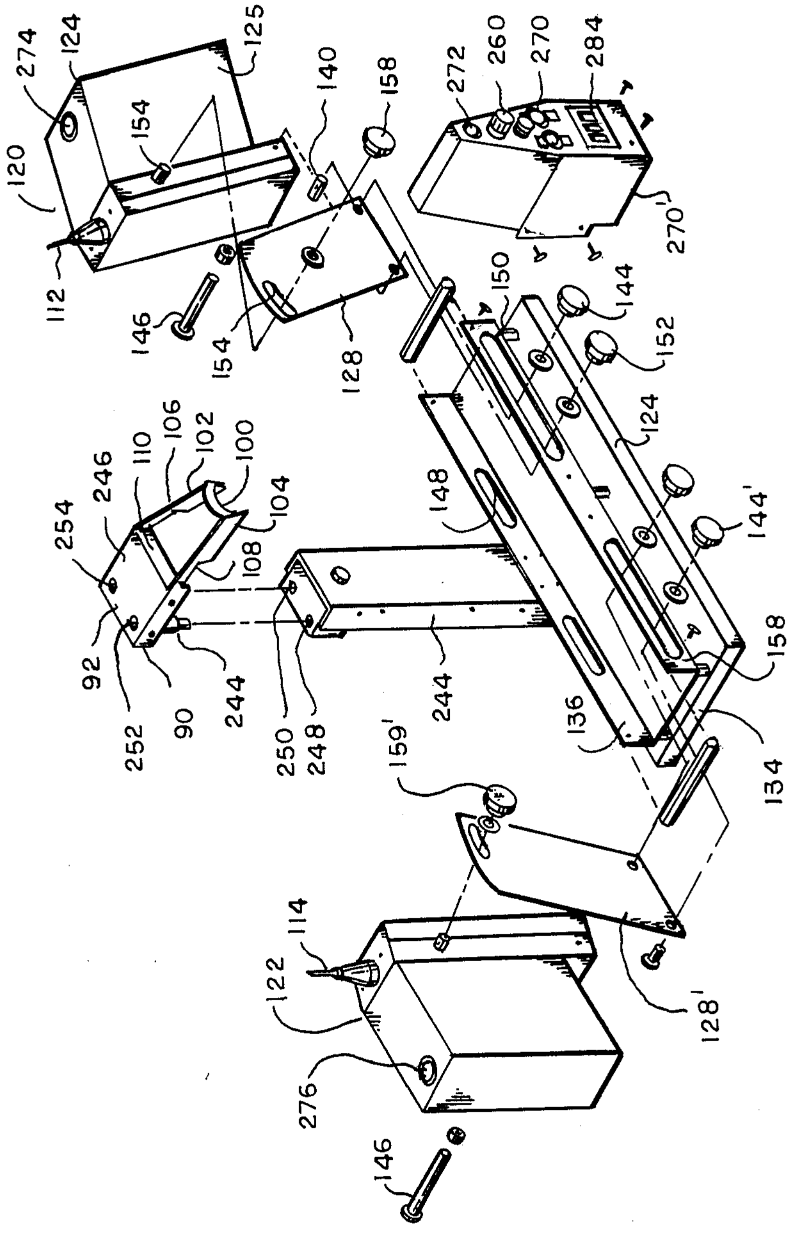
FIG. 9 shows an exploded view of the principal components shown in FIG. 5, in reduced scale.
Figure 11:
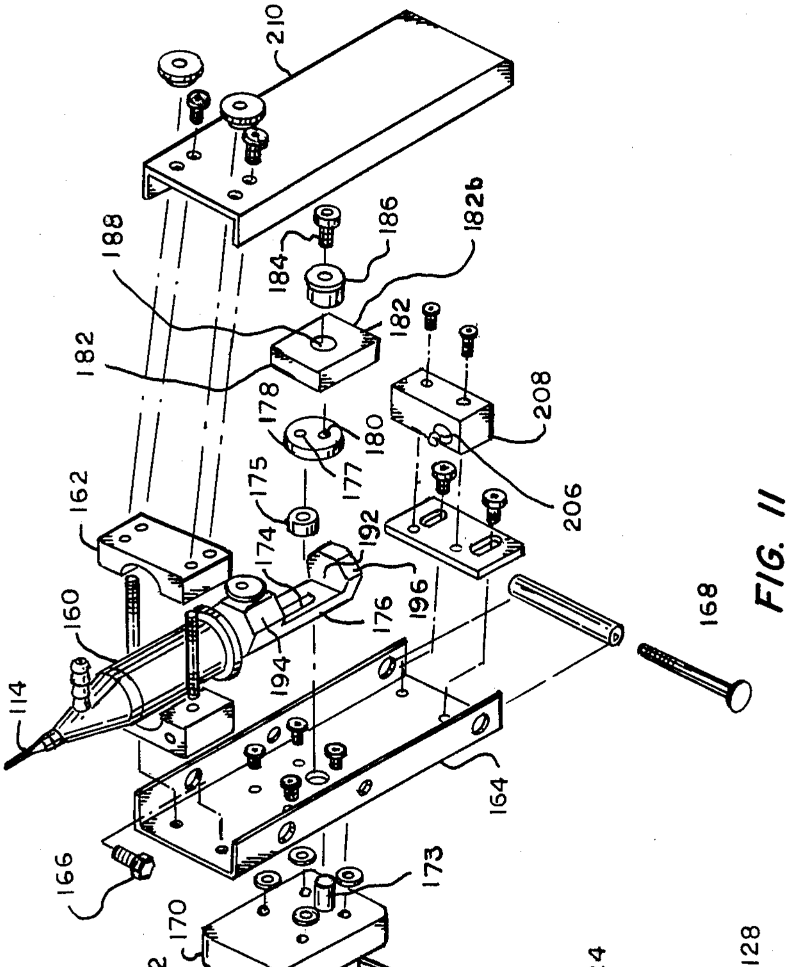
FIG. 11 shows an enlarged exploded view of the principal components of one of the injection units of the apparatus shown in FIGS. 5 and 9, as viewed from the reverse direction.

Assembly 122 mounts a syringe 160 connected to pump a fixed amount of liquid dosage to needle 114 projecting upwardly from the upper end of the syringe (FIGS. 5 and 9). As shown in FIG. 11, syringe 160 is clamped between a pair of blocks 162 secured in a channel plate 164 held by bolts 166 and 168 between the sides of cover 120. The opposite side of channel plate 164 is secured to a gear box 170 and through it to an electric motor 172 behind the gear box. A drive shaft 173 extends from the gear box through an opening in channel plate 164, and through a bushing 175 in a slot 174 in a bracket 176 secured to the lower end of syringe 160. The projecting end of shaft 173 is keyed in an opening 177 in a disk 178. Opening 177 and another opening 180 in disk 178 are oppositely eccentric to the axis of rotation of shaft 173. A slide block 182 is held in side-by-side slideable relation with disk 178 by a screw 184 fastened in disk 178 and extending through a bushing 186 to hold the bushing snugly but rotationally slideable within a central opening 188 through block 182. Bushing 186 transmits eccentric rotational drive to block 182, and this is translated into reciprocating longitudinal drive by sliding engagement of opposite parallel edges 182*a* and -*b* of block 182 with opposite parallel surfaces 190 and 192 of arms 194 and 196 of bracket 176.

Bracket arm 194 has an opening 198 (FIG. 12) for receiving the end of a piston rod 200 projecting below syringe 160 and slideable within syringe 160 in the direction of the coincident central axis of syringe 160 and rod 200. A set screw 202 through arm 194 projects into a groove 204 around the projecting end of piston rod 200, to lock bracket 174 to rod 200, and thereby cause rod 200 to reciprocate longitudinally with bracket 176 when slide block 182 alternately presses against bracket arm surfaces 190 and 192 during eccentric rotation of bushing 186 in block 182. Surfaces 190 and 192 are perpendicular to the central axes of piston rod 200 and syringe 160, so that the force exerted by block 182 on bracket 176 and piston rod 200 will be in the direction of said axes. Any sidewise force exerted through block 182 on bracket 176 and syringe 160 is substantially eliminated by the unimpeded ability of block 182 to slide sidewise against surfaces 190 and 192.

A contact button 206 is positioned beneath bracket 176 to be engaged by the bracket at the lower most end of its travel actuated by slide block 182. Button 206 actuates a switch 208 to stop the motor and operate a magnetic clutch in the motor assembly, thereby promptly stopping movement of the drive system at the end of return movement of bracket 176, syringe 160 and needle 114, when they have moved together to their lowermost positions and are ready for the next cycle.

A channel plate 210 is secured to block 162 to cover the open end of assembly cover 120.

Figure 13:
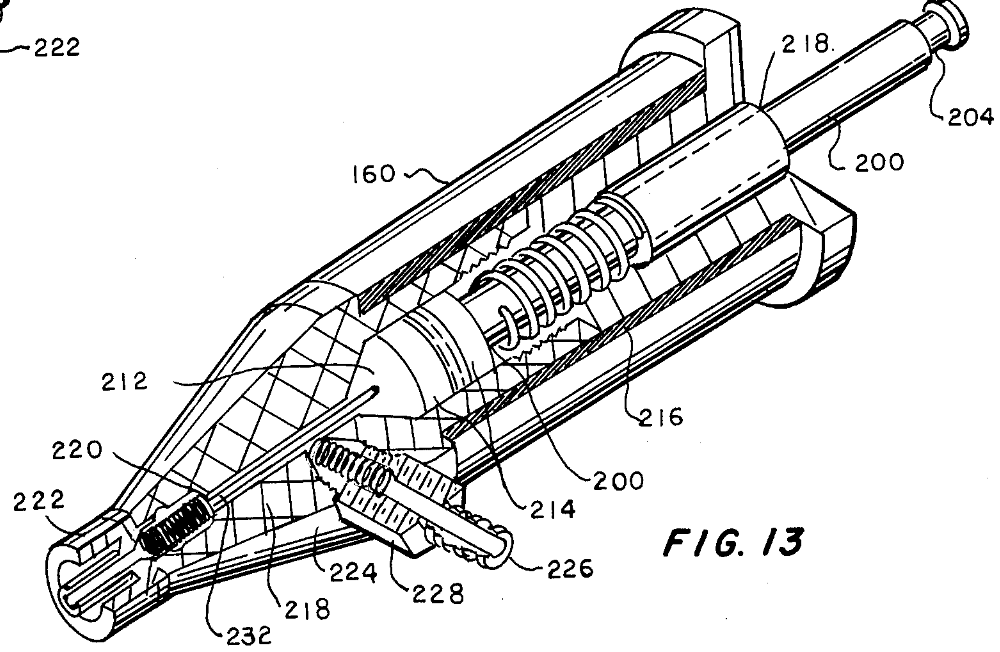
FIG. 13 shows a further enlarged and partially sectioned perspective view of the syringe shown in FIG. 12.

Syringe 160 has a cylindrical piston chamber 212 for slideably receiving piston 214 secured to the inner end of piston rod 200 (FIG. 13). A helical compression spring 216 extends around rod 200 between piston 214 and the inner end of a sleeve 218 removably mounted in a fixed position in the bore through the piston body forming the piston chamber. Piston rod 200 extends slideably through sleeve 218 and is supported by it. The piston chamber tapers conically beyond the limit of forward travel of piston 214 and then opens into a passage 218 aligned coaxially with the central axis of syringe 160 and piston rod 200. A spring loaded ball valve 220 at the outer end of passage 218 yields to permit escape of liquid under pressure from forward movement of piston 214 into the piston chamber, but positively back seats to block return flow into the piston chamber. A fitting 222 beyond valve 220 connects with a mating fitting at the base of needle 112, so that forward movement of piston 214 drives dosage liquid through passage 218 and past valve 220 for ejection through the needle.

An inlet passage 224 opens at one end transversely into passage 218 between piston chamber 212 and valve 220. The other end of passage 224 opens into a connecting passage 226 through a fitting 228 screwed into one side of syringe 160. A spring loaded ball valve 230 positively back seats to oppose out-flow of liquid from passage 218 into inlet passage 224 under pressure of liquids that are driven by piston 214 during its forward movement. However, during return movement of piston 214 the resultant reduction of pressure in the piston chamber caused valve 220 to back seat and thereby prevent inflow through needle 114 while the excess of outside atmospheric pressure over the piston chamber pressure causes valve 230 to open to admit inflow of liquid at atmospheric pressure through passages 226, 224, and 218 into the piston chamber. This loads the piston chamber with a resupply of liquid ready for the next injection, in a constant and fixed amount predetermined by the diameter and length of travel of piston 214.

Priming problems can sometimes arise due to inadvertent entry of air into the piston chamber. This can result in the piston operating against compressionable amounts of air that interfer with pumping the desired amounts of dosage liquid through needle 112. To overcome this problem a push rod 232 is mounted rigidly on piston 214 to project through the piston chamber and passage 218 far enough to engage the ball of valve 220 and unseat it during final forward movement of piston 214 (e.g., during the last two or three percent of the forward movement of the piston). This permits air in the piston chamber to be compressed during most of the forward movement of the piston, and then released past valve 220 at the end of the compression stroke, even if the air pressure had not built up sufficiently to overcome the spring loading of valve 220. Parenthetically, this improvement of expelling air from a liquid pump has other applications, such as when periodically pumping out small amounts from the bottom of diesel fuel tanks, for purposes of discharging any water which has accumulated in the fuel tank.

Figure 7:
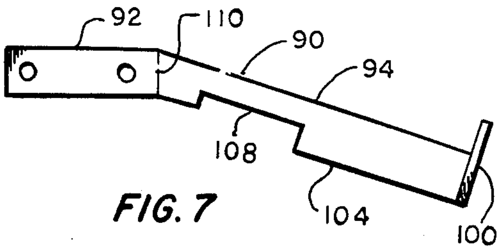
FIG. 7 shows an enlarged side view of the cradle of the apparatus shown in FIG. 5.
Figure 8:
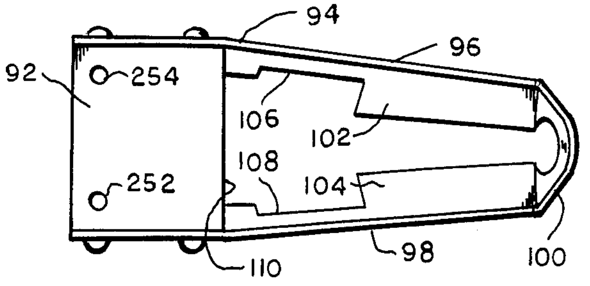
FIG. 8 shows a top plan view of the cradle shown in FIG. 7.

Returning now to the elements of the apparatus shown in FIGS. 7–9, cradle 90 is mounted on a vertical channel post 240 secured at its lower end to base plate 124 and at its upper end to a block 242. A pair of vertical posts 244 and 246 are threaded at their opposite ends to extend into a pair of openings 248 and 250 in block 248 and openings 252 and 254 in block 92, for mounting cradle 90 at a predetermined height above injection needles 112 and 114, depending on the length of the posts 244 and 246 selected for a particular series of injections. Experience so far has shown that three sizes of cradle will accomodate chickens ranging from one and a half to eight pounds. What may be referred to as size A is satisfactory for one and a half to two and a half pounds, size B is satisfactory for two and a half to four pounds, and size C is suitable for four to eight pounds. A size A cradle is illustrated in FIGS. 7–8. It has a length of about 4.355 inches between block surface 110 and end section 100. A size B cradle is similar but has a corresponding length of about 5.350 inches. A size C cradle uses a frame like that of frame 94 for a size A cradle, but carries the frame on the projecting ends of a pair of rigid arms attached to the sides of a block like that of block 92 of a size A cradle (although the block is a little larger). The block to end section distance for the size C cradle is about 6.913 inches.

Figure 10:
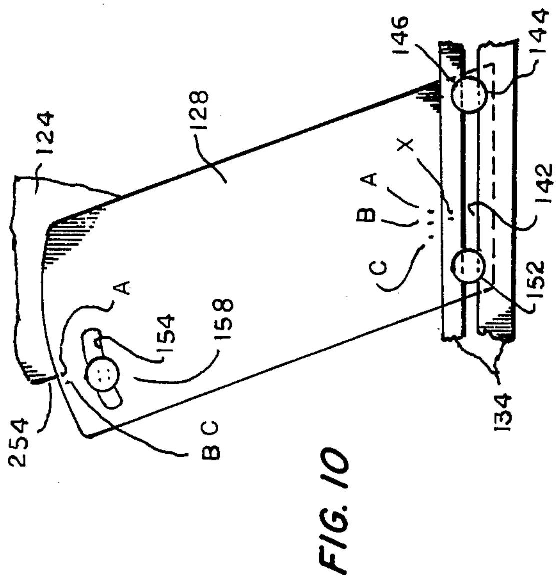
FIG. 10 shows an enlarged and broken away view of three components shown in FIG. 9.
Figure 12:
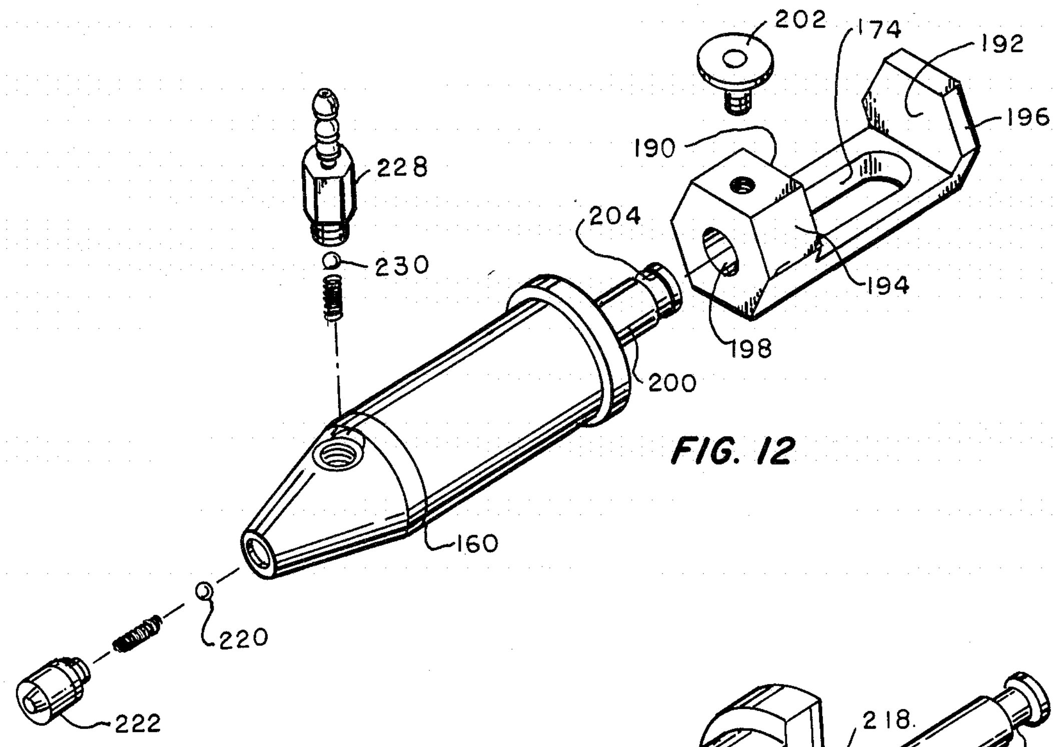
FIG. 12 shows a further enlarged perspective view of the syringe and its drive bracket from the injection unit shown in FIG. 11.

For a given one of these size ranges, the corresponding size of cradle is installed, and the lateral and angular positions of needles 112 and 114 are adjusted accordingly, as shown in FIG. 10. In the case of needle 112 this is done by moving control knobs 114 and 152 laterally until the appropriate marking A, B or C on the lower end of plate 128 matches with a mark X on flange 134, and by swinging assembly cover 124 about bolt 146 until the approporate marking A, B or C on the upper end of plate 128 matches with the adjacent edge 251 of cover 124.

Figure 6:
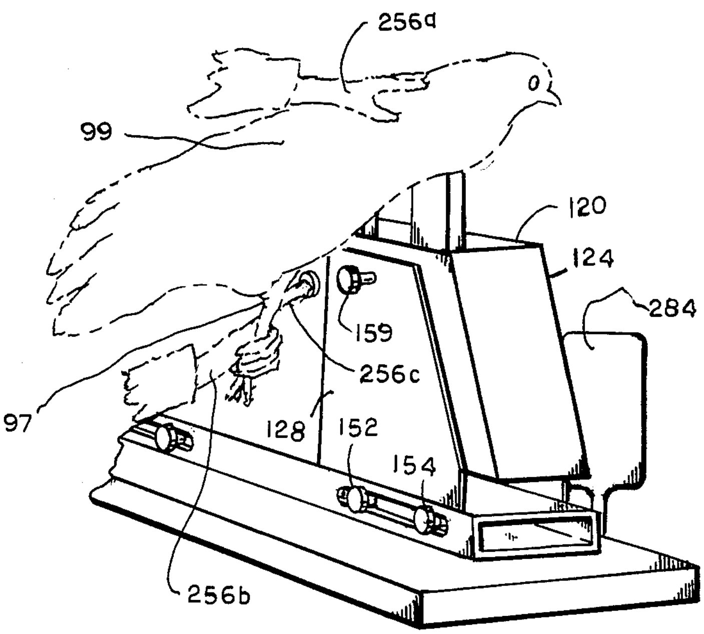
FIG. 6 shows a perspective view of a chicken in the apparatus shown in FIG. 5.
Figure 14:
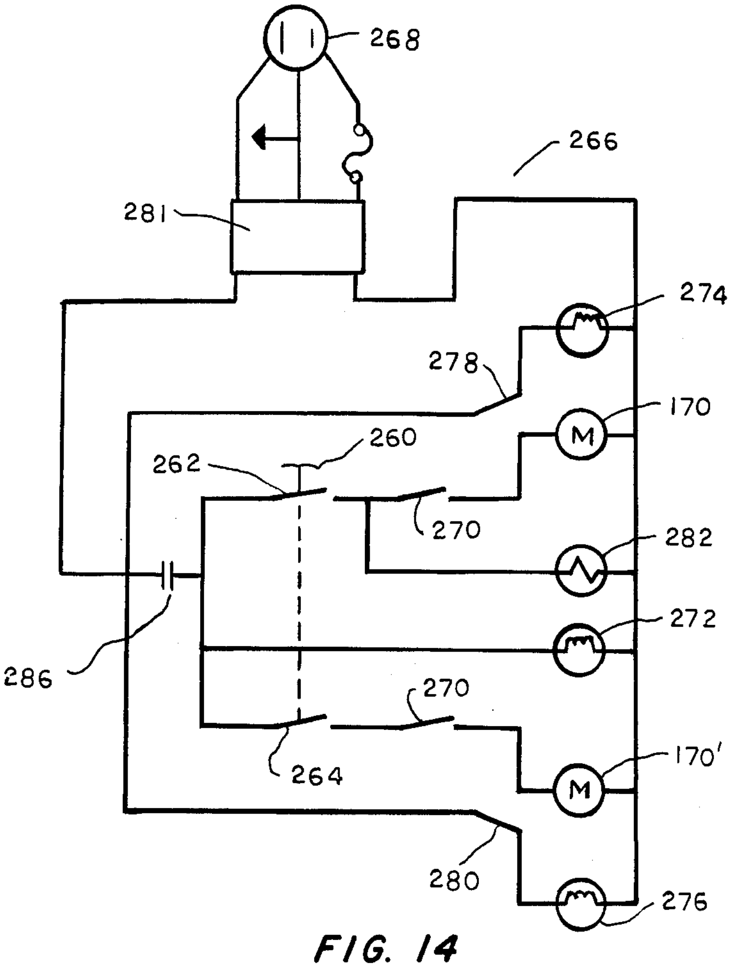
FIG. 14 shows a circuit diagram for the apparatus shown in FIGS. 5–13.

A person placing a bird on cradle 90 preferably places one hand 256*a* on top of the bird and with the other hand 256*b* holds the legs 97 of the bird substantially straight down, in a manner corresponding to that shown in FIG. 6 for a chicken. As shown in FIG. 5, a control button 260 is mounted directly below cradle 90 at a level where such leg-holding hand can readily swing the legs straight forward until part of the hand such as thumb 256*c*, presses button 260. Said pressure on button 260 causes it to close a pair of switches 262 and 264 in a control circuit 266 (FIG. 14). An electric power source 268 is connected to operate motor 170 of assembly 120 when switch 262 is closed, unless that motor has been inactivated by the operator's opening of a switch 270 (when only one injection needle is to be used). Power source 268 is also connected to operate the corresponding motor 170' of assembly 122 when switch 264 is closed, unless the motor has similarly been inactivated by a switch 270' corresponding to switch 270. A red warning light 272 is turned on while power is being supplied to either or both of the motors 170 and 170', as a danger signal to the operator to avoid coming within range of movement of needles 112 and 114. A green light 274 is mounted in top of the cover of assembly 120, and a green light 276 in the top of the cover of assembly 122, where the operator can see them while holding a bird in cradle 90. These green lights remain on as long as power is connected to circuit 264, except when their respective control switches 278 and 280 are open. Control switch 278 is automatically opened when either or both of switches 262 and 270 are closed, and switch 280 is automatically opened when either or both of switches 264 and 270' are closed. Thus, each of the green lights 274 and 276 are on when the assembly on which the light is mounted is ready for operation, but not while its assembly has been switched off, or while either or both of the motors 170 and 170' are powered.

A ground fault interrupt unit 281 is connected between power source 268 and circuit 266 to prevent accidental shock to the operator due to faulty circuit grounding.

A counter 282 with a visible indicator 284 is connected in the circuit to determine the number of times either of the motors is powered, as this correlates with the amount of dosage liquid being used and hence when the supply bottle should be replaced. An automatic cut off switch 286 inactivates the motors when the count passes a preset limit approximating the amount in each successive supply bottle (such as bottle 284 in FIG. 6).

While present preferred practices and embodiments of the invention have been illustrated and described, it may be otherwise variously embodied and practiced within the scope of the following claims.

We claim:

1. Apparatus for injecting breast muscle tissue of a bird, comprising breast supporting structure adapted to support a bird with its breast keel bone pointing downwardly and extending lengthwise of the structure, said structure including means to engage the sides and opposite end portions of the bird's body for determining its sidewise and lengthwise position in the structure, and said structure being adapted to permit the legs of a bird so positioned in the structure to extend downwardly and close enough together to be gripped by one hand of a person operating the apparatus, means holding said supporting structure stationary during operation of the apparatus, a pair of injection needles, separate means mounting the respective needles to move upwardly from their respective starting positions and convergently toward and into injection positions in breast muscle tissue on opposite sides of the keel bone of a bird so positioned in said supporting structure, separate means connected to move said needles from said starting positions into said injection positions and back to said starting positions, and means to cause emissions of liquid from the needles while substantially at said injection positions.

2. Apparatus according to claim 1, comprising hand operable means to start operation of the means move to the needles from their starting positions, said hand operable means being positioned beneath said supporting structure where a person's hand holding the downwardly extending legs of a bird in the supporting structure can at the same time operate said hand operable starting means.

3. Apparatus according to claim 1, including means to inactivate the means to move one of the needles while permitting the other needle moving means to function.

4. Apparatus according to claim 1, including means for laterally and angularly adjusting the positions of each of said needle mounting means, whereby the paths of movement of the needles may be adjusted accordingly when substantially different sizes of birds are to be injected.

5. Apparatus according to claim 1, including an electric circuit connected to operate both of said needle moving means, means in said circuit to produce a visible light on the mounting means for each needle, and means to cause each of said light means to light when said circuit is connected to a power source but not while the circuit is connected to operate the moving means for the needle or the mounting means associated with the light, whereby each light means when on indicates readiness for operation of the associated needle, and when off indicates movement of the needle is in progress or lack of a power source connected to the circuit.

6. Apparatus according to claim 5, including means in said circuit to produce a visible warning light while movement of either or both of the needles is in progress.

7. Apparatus according to claim 1, in which said mounting means for each needle includes a syringe body attached to the needle, a syringe piston and piston rod for the syringe body, a motor for actuating the syringe piston rod and piston, and drive means connecting the motor and piston rod, said drive means comprising a slide block, means rotatable by the motor to impart eccentric motion to the slide block having a pair of parallel oppositely facing surfaces, and means attached to the piston rod and having a pair of opposed parallel surfaces slideable against said parallel surfaces of the slide block, whereby longitudinal reciprocating motion with a minimum of side thrust is emparted to the piston rod.

8. Apparatus according to claim 1, in which said mounting means for each needle includes a syringe body attached to the a piston reciprocable within the piston body, an outlet passage through the body from the piston chamber to the inlet of the attached needle, a spring-loaded valve in said passage adapted to yield resiliently when the piston moves forward to force liquid from the piston chamber to the needle, and to back-seat positively to prevent return flow of liquid from the needle, and an elongated member mounted on and extending from the piston into said passage toward said valve, said elongated member being long and rigid enough to engage and force open the valve near the end of forward movement of the piston, whereby any air caught in the piston chamber may be discharged therefrom.

9. Apparatus for injecting the breast muscles of a bird simultaneously at different angles of thrust of the injection needles, comprising a pair of injection needles, means to hold a bird's breast stationary in a predetermined position relative to the needles, means mounting the needles to reciprocate in paths converging towards opposite sides of the keel bone of a bird's breast held in said position, means to adjust said holding means to cause the needles to penetrate to the muscle tissue on the opposite sides of the keel bone, drive means to move the needles at the same time into the breast muscle tissue, to retract them, and to eject fluid from both needles at substantially the ends of their movements into the breast muscle tissue, and means to start the drive means, said starting means being positioned to be activated by a hand grasping the legs of a bird whose breast is held in said predetermined position.

10. A method of injecting a bird comprising the steps of holding the bird in a fixed position by placing the bird on a fixed cradle with its legs extending downwardly, using one hand to grasp said downwardly extending legs while initiating the step of simultaneously moving a pair of injection needles at converging angles into the breast muscles tissue on opposite sides of the keel bone of the bird, and injecting a liquid dosage into said tissue through said needles.

* * * * *